United States Patent
Kuusela et al.

(10) Patent No.: US 12,045,988 B2
(45) Date of Patent: Jul. 23, 2024

(54) USING RADIATION DOSE INFORMATION FOR AUTOMATIC ORGAN SEGMENTATION MODEL TRAINING

(71) Applicant: SIEMENS HEALTHINEERS INTERNATIONAL AG, Steinhausen (CH)

(72) Inventors: Esa Kuusela, Espoo (FI); Hannu Laaksonen, Helsinki (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 651 days.

(21) Appl. No.: 17/214,348

(22) Filed: Mar. 26, 2021

(65) Prior Publication Data

US 2022/0309673 A1 Sep. 29, 2022

(51) Int. Cl.
| | | |
|---|---|---|
| *G06T 7/11* | (2017.01) | |
| *G06N 20/00* | (2019.01) | |
| *G16H 20/40* | (2018.01) | |
| *G16H 30/20* | (2018.01) | |

(52) U.S. Cl.
CPC .............. *G06T 7/11* (2017.01); *G06N 20/00* (2019.01); *G16H 20/40* (2018.01); *G16H 30/20* (2018.01); *G06T 2207/20081* (2013.01)

(58) Field of Classification Search
CPC . G06T 7/11; G06T 2207/20081; G16H 20/40; G16H 30/20; G06N 20/00
See application file for complete search history.

(56) References Cited

U.S. PATENT DOCUMENTS

| | | | | |
|---|---|---|---|---|
| 10,032,250 | B2 * | 7/2018 | Mazurkewitz | G06T 7/74 |
| 10,888,711 | B2 * | 1/2021 | Nordström | A61N 5/1031 |
| 11,367,185 | B2 * | 6/2022 | Yu | G16H 50/20 |
| 11,497,557 | B2 * | 11/2022 | Haslam | G06T 7/0012 |
| 11,615,879 | B2 * | 3/2023 | Do | G06V 20/20 |
| | | | | 382/128 |

(Continued)

OTHER PUBLICATIONS

Gonglei Shi et al: "Marginal loss and exclusion loss for partially supervised multi-organ segmentation", ARXIV.org, Cornell University Library, 201 Olin Library, Ithaca, NY, 14853, Jul. 8, 2020, XP081717907.

(Continued)

*Primary Examiner* — Gregory M Desire
(74) *Attorney, Agent, or Firm* — FOLEY & LARDNER LLP

(57) ABSTRACT

Disclosed herein are systems and methods for training a machine learning model for automatic organ segmentation. A processor receives an image of one or more pre-contoured organs, the image comprising a plurality of voxels. The processor executes a machine learning model using the image to output predicted organ labels for the plurality of voxels of the image. The processor determines differences between corresponding predicted organ labels and expected organ labels for the plurality of voxels. The processor determines radiation dose levels that correspond to the plurality of voxels of the image. The processor determines weights for the plurality of voxels based on the radiation dose levels of the respective voxels. The processor then trains the machine learning model based on the differences and the weights for the plurality of voxels.

20 Claims, 5 Drawing Sheets

(56) References Cited

U.S. PATENT DOCUMENTS

2021/0177295 A1*  6/2021  Maximo ............... G06T 7/0012
2022/0028085 A1*  1/2022  Vasilev ................. G16H 30/40

OTHER PUBLICATIONS

ISR and Written Opinion on PCT Application PCT/EP2022/057279, Sep. 20, 2022 (13 pages).

Jianpeng Zhang et al.: "DoDNet: Learning to segment multi-organ tumors from multiple partially labeled datasets", ARXIV.org, Cornell University Library, 201 Olin Library, Ithaca, NY, 14853, Nov. 20, 2020, XP081818535.

Ke Yan et al: "Learning from Multiple Datasets with Heterogeneous and Partial Labels for Universal Lesion Detection in CT", ARXIV.org, Cornell University Library, 201 Olin Library, Ithaca, NY, 14853, Sep. 5, 2020, XP081757445.

Verma Yashaswi et al: "Image Annotation by Propagating Labels from Semantic Neighbourhoods", ARXIV.org, Cornell University Library, 201 Old Library, Ithaca, NY, 14853, vol. 121, No. 1, Jul. 12, 2016, pp. 126-148, XP036133974.

Zhang Guobin et al: "Automatic segmentation of organs at risk and tumors in CT images of lung cancer from partially labeled datasets with a semi-supervised conditional nnU-Net", Computer Methods and Programs in Biomedicine, Elsevier, Amsterdam, NL, vol. 211, Sep. 15, 2021, XP086843205.

* cited by examiner

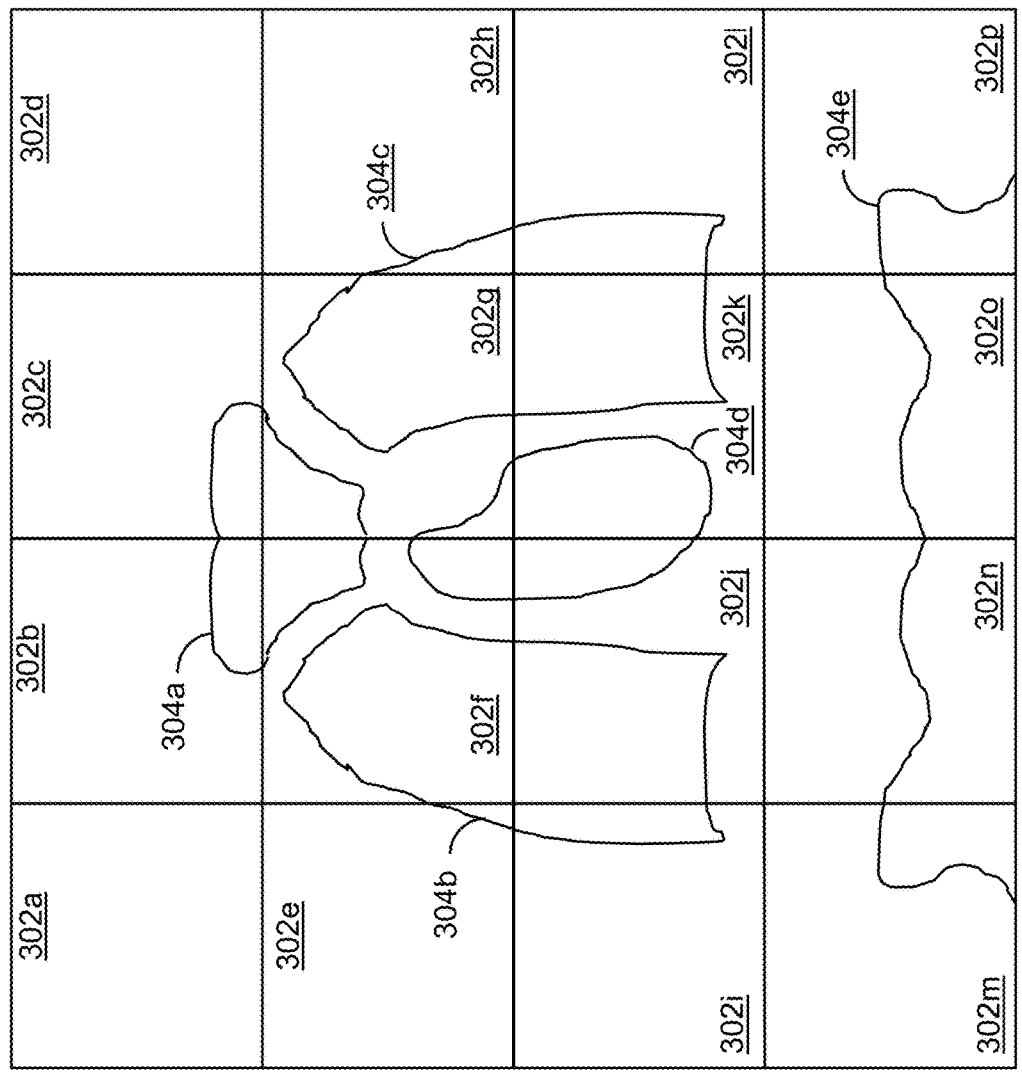

| W=0 | 302a | W=1 | 302e | W=1 | 302i | W=0 | 302m |
|---|---|---|---|---|---|---|---|
| W=0 | 302b | W=1 | 302f | W=1 | 302j | W=0 | 302n |
| W=0 | 302c | W=1 | 302g | W=1 | 302k | W=0 | 302o |
| W=0 | 302d | W=1 | 302h | W=1 | 302l | W=0 | 302p |

FIG. 3B

USING RADIATION DOSE INFORMATION FOR AUTOMATIC ORGAN SEGMENTATION MODEL TRAINING

TECHNICAL FIELD

This application relates generally to using radiation dose information for a set of pre-contoured images to train a machine learning model for automatic organ segmentation.

BACKGROUND

Radiotherapy (radiation-based therapy) is used as a cancer treatment to emit high doses of radiation that can kill cells or shrink a tumor. The target region of a patient's body that is intended to receive radiation (e.g., a tumor) is referred to as the planning target volume (PTV). The goal is to deliver enough radiation to the PTV to kill the cancerous cells during the radiotherapy treatment. However, other organs or anatomical regions that are adjacent to, or surrounding, the PTV can be in the way of radiation beams and can receive enough radiation to damage or harm such organs or anatomical regions. These organs or anatomical regions are referred to as organs at risk (OARs). Usually, for radiation therapy treatment planning (RTTP), a physician or a radiologist identifies both the PTV and the OARs prior to radiotherapy using, for example, computed tomography (CT) images, magnetic resonance imaging (MM) images, positron emission tomography (PET) images, images obtained via some other imaging modality, or a combination thereof. For instance, the physician or the radiologist may manually mark the PTV and/or the OARs on the medical images of the patient.

It can be important to accurately identify organs in images so physicians can accurately configure radiotherapy machines to direct radiation to the right organs without affecting the organs at risk. Typically, to account for such risks, a physician may use a contouring software to outline images of individuals based on what the physician believes to be are the individual's organs. Such a process may take a large amount of time and may result in inaccuracies given the poor quality some images may have. Inaccurate contouring may cause a radiotherapy machine to direct radiation to an OAR or another region of a person entirely during radiotherapy treatment. For example, a physician may incorrectly outline an organ within an image when determining field geometry settings to use to configure a radiotherapy machine providing treatment to a patient. Thus, typical methods of contouring images may result in inaccurate results and, in some cases, result in improper patient treatment.

SUMMARY

For the aforementioned reasons, there is a desire for a system that can train a computer model (e.g., a machine learning model) to accurately contour images of individuals to indicate the locations of the organs, bones, and/or any tumors on the organs or bones. However, systems that use machine learning models to contour images often have issues generating training data sets that either have enough contoured images to train the respective models or have accurate training data. For example, while a clinician may be careful to contour images of a patient in areas that are being treated, the clinician may be less careful or fail to contour other areas of the images. Conventional systems may account for these deficiencies by discarding the poorly contoured images or by simply feeding these images into models for training. But such methods may result in poorly trained models either because not enough training data is available (which may be a common problem for models trained based only on images captured at a clinic local to the machine learning model) or because the models are improperly biased or weighted based on the inaccurate training data. Thus, there is a need to properly curate training data without discarding potential training data while ensuring the models are accurately trained.

To overcome these deficiencies, it is desirable to train a machine learning model using radiation dose information that corresponds to the images in the training data set. Instead of discarding inaccurate or partially inaccurate contoured images, the systems and methods described herein may weight different portions of the image based on the radiation dosage that was applied to different areas of the depicted patient. Because physicians may be more likely to contour areas of images that depict organs that are receiving treatment for RTTP, the system may weight pixels or voxels, depending on if the image is two-dimensional or three-dimensional, of the image based on the radiation dosage that was applied to the organs that correspond to the pixels or voxels. The system may weight pixels or voxels of the image that correspond to a high radiation dosage (e.g., a dosage that exceeds a threshold) with a high weight because such pixels or voxels are likely to correlate with a higher degree of accuracy. Because the system may perform such a weighting technique for each area of an image, the system may no longer need to discard images that have been partially labeled or that have been labeled by a practitioner with a tendency to only accurately label portions of individual images, and may further ensure each image may be used for accurate training.

In one embodiment, a method for training a machine learning model for automatic organ segmentation comprises receiving, by a processor, an image of one or more pre-contoured organs, the image comprising a plurality of voxels; executing, by the processor, a machine learning model using the image to output predicted organ labels for the plurality of voxels of the image; determining, by the processor, differences between corresponding predicted organ labels and expected organ labels for the plurality of voxels; determining, by the processor, radiation dose levels that correspond to the plurality of voxels of the image; determining, by the processor, weights for the plurality of voxels based on the radiation dose levels of the respective voxels; and training, by the processor, the machine learning model based on the differences and the weights for the plurality of voxels.

In another embodiment, a system for training a machine learning model for automatic organ segmentation comprises a processor configured to execute instructions stored on a non-transitory computer-readable medium to receive an image of one or more pre-contoured organs, the image comprising a plurality of voxels; execute a machine learning model using the image to output predicted organ labels for the plurality of voxels of the image; determine differences between corresponding predicted organ labels and expected organ labels for the plurality of voxels; determine radiation dose levels that correspond to the plurality of voxels of the image; determine weights for the plurality of voxels based on the radiation dose levels of the respective voxels; and train the machine learning model based on the differences and the weights for the plurality of voxels.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIGS. 3A-B illustrate an example weighted pre-contoured training image, according to an embodiment.

DETAILED DESCRIPTION

Figure 1:
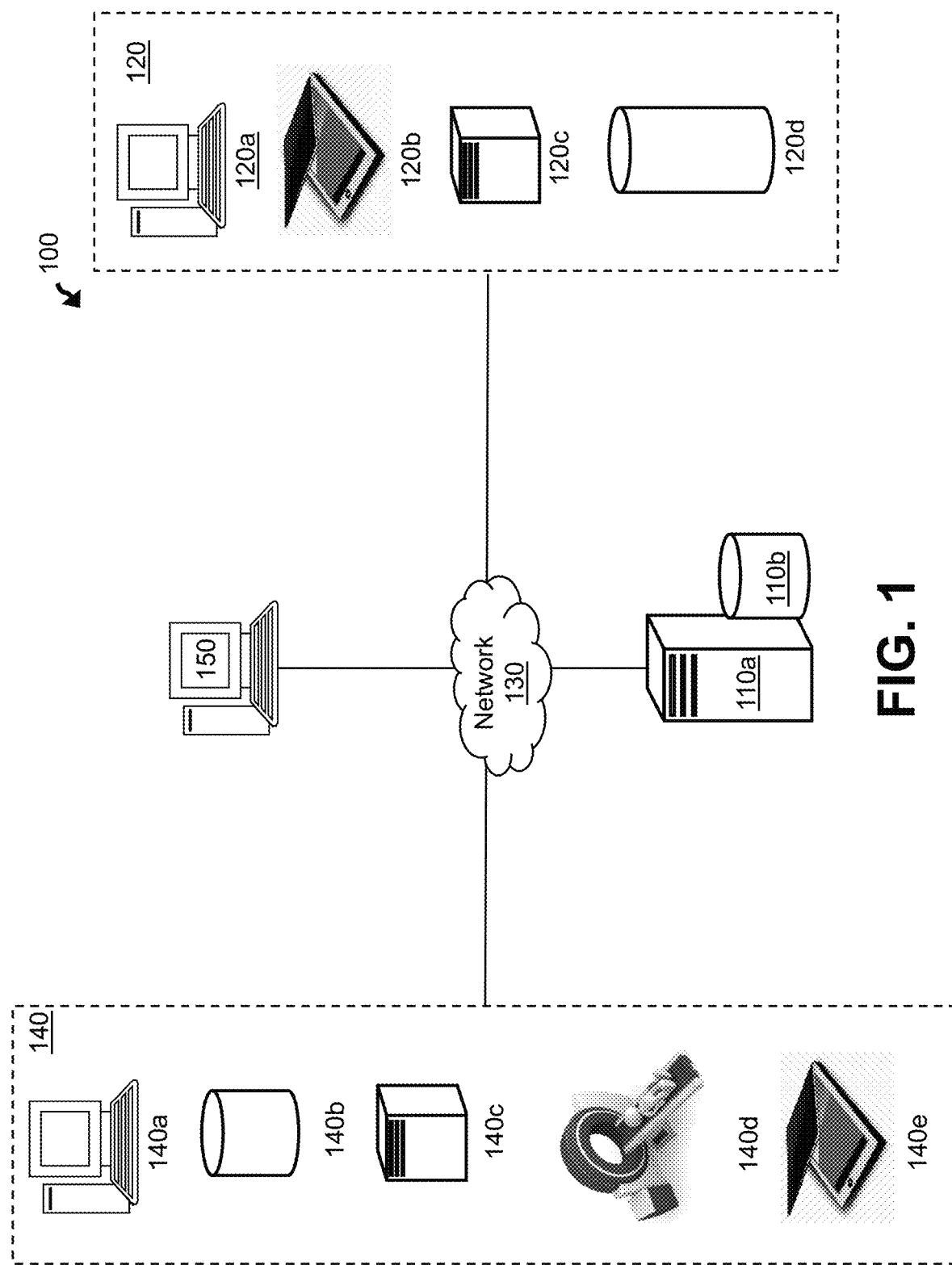
FIG. 1 illustrates components of an organ contouring segmentation system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Supervised learning machine learning models, such as convolutional neural networks (CNN) models, have been shown to be a powerful approach to automatic organ segmentation. In this machine learning approach, a machine learning model may be trained using a set of CT images (or other images such as Mill or PET images) and labels that correspond to organs within the CT images. Such training often requires a large number of training images to adequately train the models. For example, training a machine learning model to accurately contour organs from images may require in the order of a few hundred cases.

It is common for a clinical database to contain large sets of pre-contoured images, but such sets of pre-contoured images may contain images with inaccurate labels, which may affect the accuracy of such training. To resolve such accuracy issues, an operator may manually curate the training sets, removing any images that include inaccurate labels or that otherwise have areas within the image that may improperly bias the machine learning model towards making poor predictions. Such curation can be an expensive process and is often the bottleneck of training new machine learning models or adjusting existing models to better reflect local nuances in organ contouring.

One particular problem related to the quality of the existing training in a clinical database is that when organs of the images in the training were originally contoured for the purpose of radiotherapy treatment planning, a clinician usually had in mind "a region of interest" where the organ contouring needed to be accurate to achieve a quality plan. Outside of the region of interest, however, the technician may not have put forth as much effort toward properly contouring the image, which could often result in the technician improperly labeling those areas of the image or not labeling those areas at all. For example, a technician may only partially contour an organ (e.g., a spine) because the organ may be large and a portion of the organ may be far outside of the region of interest. Such images may be removed from a training set for having inaccurate data or may be used for training and cause the trained model to be improperly trained.

By implementing the systems and methods described herein, a system may resolve the aforementioned training deficiencies by removing the need to curate training data sets and instead weight individual pixels or voxels of the images based on the amount of radiation dosage that was applied to the area of a person depicted by the respective pixels or voxels. The dose information may be used to estimate the locations the organ contouring within the image has been the most accurate. The system may enable a weighted training method that emphasizes pixels or voxels that are associated with areas of a person in which the most radiation was applied, and de-emphasize, or neglect completely, pixels or voxels that are associated with areas where little or no radiation was applied. The system may use the dosage emphasis as a spatial weighting factor so models can be trained using partial organ information and handle a gradual de-emphasis in any weight adjustments as the expected accuracy of organ segments decreases.

Advantageously, by implementing the systems and methods described herein, a system may automatize training set selection or otherwise train machine learning models for automatic organ contouring. Moreover, the solution may enable the system to use partially contoured organs in a training set without removing images from the set, without adjusting the training to only focus on accurately contoured regions of images, and/or without improperly biasing the model's training.

As will be described below, a server (referred to herein as an analytics server) can train a neural network or other machine learning model to contour images of organs for RTTP planning. In a non-limiting example, the server may obtain a training set of pre-contoured (e.g., labeled) images of organs of individuals that received radiotherapy treatment. For each image of the set, the server may determine the radiation dosage that was applied to the areas of the depicted individual's organs during the respective radiotherapy treatment. The server may determine training weights for pixels or voxels of the images based on the radiation dosage that was applied to areas of the organs that the pixels or voxels depict. The server may apply the training set to a machine learning model and use the determined weights to train the model to contour organs in new images. FIG. 1 is a non-limiting example of components of a system in which the analytics server operates.

FIG. 1 illustrates components of an organ contouring segmentation system 100. The system 100 may include an analytics server 110a, a system database 110b, electronic data sources 120a-d (collectively electronic data sources 120), end-user devices 140a-e (collectively end-user devices 140), and an administrator computing device 150. The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, for example, a GSM (Global System for Mobile Communications), CDMA (Code Division Multiple Access), or an EDGE (Enhanced Data for Global Evolution) network.

The system 100 is not confined to the components described herein and may include additional or other components, not shown for brevity, which are to be considered within the scope of the embodiments described herein.

The analytics server 110a may generate and display an electronic platform configured to use various computer models (including artificial intelligence and/or machine learning models) to contour two-dimensional and/or three-dimensional images with labels indicating the organs that different pixels or voxels of the image represent or depict. The electronic platform may include graphical user interfaces (GUI) displayed on each electronic data source 120, the end-user devices 140, and/or the administrator computing device 150. An example of the electronic platform generated and hosted by the analytics server 110a may be a web-based application or a website configured to be displayed on different electronic devices, such as mobile devices, tablets, personal computers, and the like. In a non-limiting example, a physician operating the physician device 120b may generate a training data set by contouring a set of images (e.g., CT scans or other images) with labels indicating the depicted organs. The physician may also generate a record of treatment attributes for treating the individuals that are depicted in the images. The physician may upload RTTP for the individuals indicating the treatment attributes for each respective individual's treatment and the labeled images that correspond to the individual's RTTP. The physician device 120b may receive the contoured images and/or RTTP and transmit images and the plans to the analytics server 110a or store the images and/or plans locally. The analytics server 110a or the physician device 120b may utilize the systems and methods described herein to determine radiation dosage information for individual pixels or voxels of the images based on the corresponding RTTP, assign weights to the pixels or voxels based on the radiation dosage information, and train the computer models based on the weights.

As described herein, treatment attributes may be or include any attributes related to treating patients at a radiotherapy clinic and/or using a radiotherapy machine. Treatment attributes may include, but are not limited to, different treatment modalities, field geometry settings for external beam radiotherapy, side effect predictions, organ and/or tumor segmentation, machine therapy attributes, dosage administration attributes (e.g., dosage amount), treatment frequency, treatment timing, etc.

The analytics server 110a may host a website accessible to users operating any of the electronic devices described herein (e.g., end-users), where the content presented via the various webpages may be controlled based upon the roles and/or viewing permissions of each particular user. The analytics server 110a may be any computing device comprising a processor and non-transitory machine-readable storage capable of executing the various tasks and processes described herein. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each electronic data source 120 and/or end-user devices 140. Different users may use the website to view and/or interact with predicted results from the learning models.

The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may also store data associated with each user operating one or more electronic data sources 120 and/or end-user devices 140. The analytics server 110a may use the data to weigh interactions while training various AI models accordingly. For instance, the analytics server 110a may indicate that a user is a medical professional whose inputs may be monitored and used to train the machine learning or other computer models described herein.

The analytics server 110a may generate and host webpages based upon a particular user's role within the system 100. In such implementations, the user's role may be defined by data fields and input fields in user records stored in the system database 110b. The analytics server 110a may authenticate the user and may identify the user's role by executing an access directory protocol (e.g. LDAP). The analytics server 110a may generate webpage content that is customized according to the user's role defined by the user record in the system database 110b.

The analytics server 110a may receive RTTP data (e.g., patient and treatment data) from a user or retrieve such data from a data repository, analyze the data, and display the results on the electronic platform. For instance, in a non-limiting example, the analytics server 110a may query and retrieve medical images from the database 120d and combine the medical images with RTTP data received from a physician operating the physician device 120b. The analytics server 110a may then use various models (stored within the system database 110b) to analyze the retrieved data. The analytics server 110a may then display the results via the electronic platform on the electronic physician device 120b, the end-user devices 140, and/or the administrator computing device 150, The electronic data sources 120 may represent various electronic data sources that contain, retrieve, and/or input data associated with RTTP (e.g., patient data and treatment data). For instance, the analytics server 110a may use the clinic computer 120a, physician device 120b, server 120c (associated with a physician and/or clinic), and database 120d (associated with the physician and/or the clinic) to retrieve/receive RTTP data associated with a particular patient's treatment plan.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110*a*. Specifically, the end-user devices 140 may include clinic computer 140*a*, clinic database 140*b*, clinic server 140*c*, a medical device, such as a CT scan machine, radiotherapy machine (e.g., a linear accelerator or a cobalt machine), and the like (140*d*), and a clinic device 140*e*.

The administrator computing device 150 may represent a computing device operated by a system administrator. The administrator computing device 150 may be configured to display data retrieved, treatment attributes generated by the analytics server 110*a* (e.g., various analytic metrics and/or field geometry) where the system administrator can monitor various models utilized by the analytics server 110*a*, electronic data sources 120, and/or end-user devices 140; review feedback; and/or facilitate the training of the machine learning models that are maintained by the analytics server 110*a*.

In operation, a physician may access an application executing on the physician device 120*b* and input RTTP data (e.g., patient information, patient diagnosis, radiation therapy treatment attributes, etc.). The analytics server 110*a* may use a patient identifier to query patient data (e.g., patient anatomy and/or medical images) from the electronic data sources 120. The analytics server 110*a* may then utilize the systems and methods described herein to contour the medical images from the patient data, generate configuration data to control the medical device 140*d* based on the contoured medical images, and generate an optimized/uniform RTTP and display the results onto the physician device 120*b*, clinic computer 140*a*, and/or the medical device 140*d* (e.g., a display screen of the radiotherapy machine).

For example, the analytics server 110*a* may be in communication (real-time or near real-time) with the medical device 140*d*. A server/computer hosting the medical device 140*d* can adjust the medical device 140*d* based on contoured images that the analytics server 110*a* either receives from an external source or that the analytics server 110*a* contours itself using machine learning models stored in memory of the analytics server 110*a*. For instance, the analytics server 110*a* may execute a machine learning model to contour an image to indicate the locations of different organs of a person that is currently receiving radiotherapy treatment. The analytics server 110*a* may identify the locations of the organs from the image and transmit instructions to the medical device 140*d* to indicate how to operate the gantry and other field geometry settings for the medical device 140*d* to use to provide radiotherapy treatment to the individual. The analytics server 110*a* may transmit instructions to the medical device 140*d* indicating any number or type of treatment attributes (e.g., field geometry settings) to facilitate such treatment based on the contoured image. In some cases, the analytic server 110*a* may transmit contoured images to the medical device 140*d* and the medical device 140*d* may generate field geometry settings to treat the corresponding patient using intrinsic processes.

As described above, the analytics server 110*a* may store machine learning models (e.g., neural networks, random forest, support vector machines, etc.) in memory. The analytics server 110*a* may retrieve the models and train the machine learning models to predict labels for two-dimensional and/or three-dimensional images (e.g., CT scans) of individuals. To do so, the analytics server 110*a* may use a data set of pre-contoured images and RTTP plans that correspond to the pre-contoured images (e.g., RTTP plans for treatment of the individuals depicted in the images). For example, the analytics server 110*a* may execute one or more machine learning models using the pre-contoured images of the individuals and identify confidence scores for one or more labels for pixels or voxels of the pre-contoured images. The analytics server 110*a* may retrieve the RTTP plans that correspond to the images and determine an amount of radiation that was applied or that will be applied to different areas of the respective patient during treatment. The amount of radiation may correspond to the amount of radiation that is applied during radiotherapy treatment and/or the amount of radiation that is applied during a scan (e.g., an X-Ray or a CT scan). For individual pixels or voxels, the analytics server 110*a* may apply a weighting function to the radiation dosage of the pixel or voxel to determine a training weight. The training weight may be a binary or non-binary value depending on the weighting function that the analytics server 110*a* is configured to apply. The analytics server 110*a* may determine a loss function based on the determined weight and a difference between the predicted confidence scores and the ground truth for each of the pixels or voxels of the image. The data processing system may use the determined loss function to train the machine learning models to more accurately predict labels or contour for images.

Figure 2:
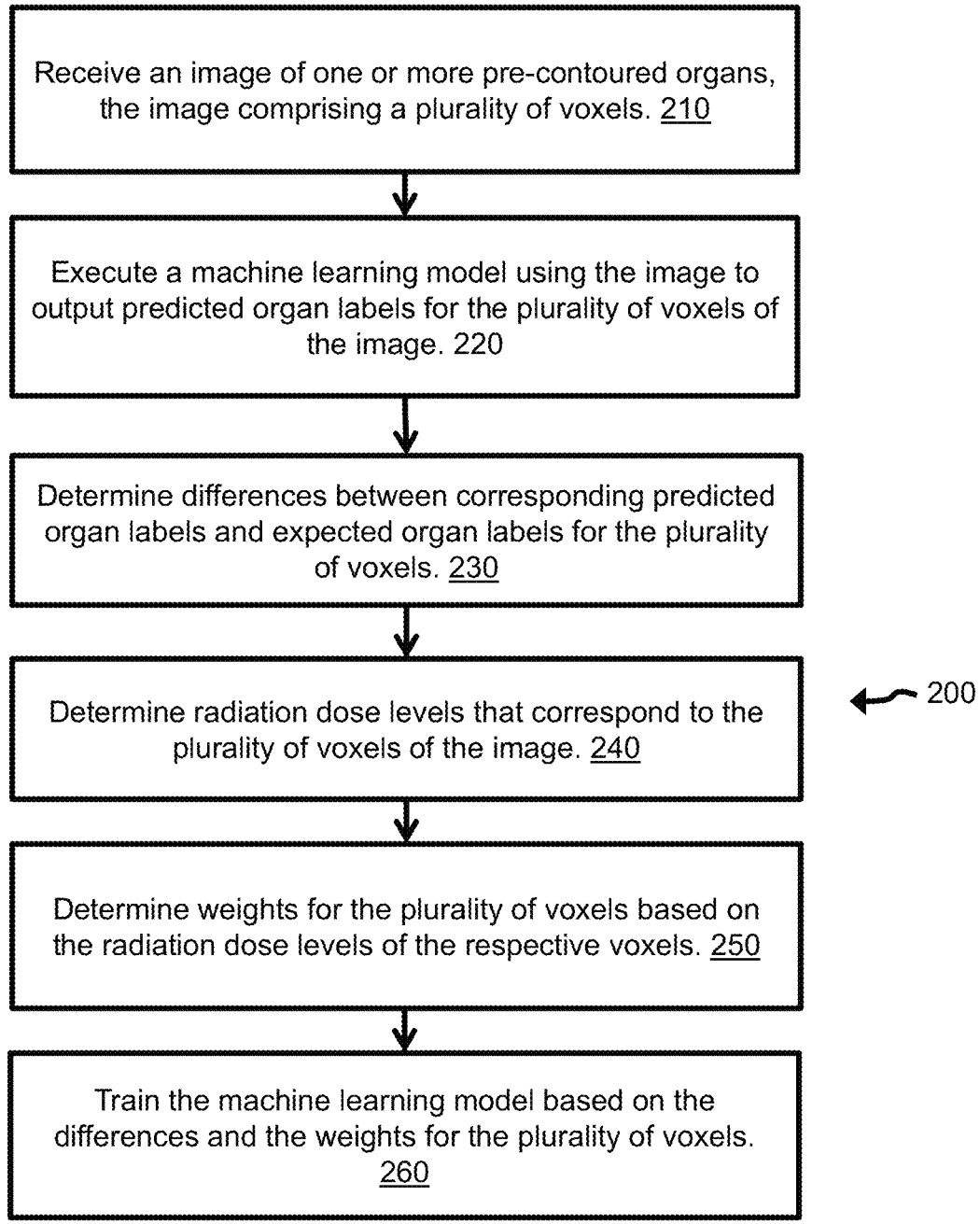
FIG. 2 illustrates a flow diagram of a process executed in an organ contouring segmentation system, according to an embodiment.

FIG. 2 illustrates a flow diagram of a process executed in an organ contouring segmentation system, according to an embodiment. The method 200 may include steps 210-260. However, other embodiments may include additional or alternative steps, or may omit one or more steps altogether. The method 200 is described as being executed by a data processing system (e.g., a computer similar to the analytics server 110*a*, the data source 120, or the end-user device 140 described in FIG. 1). However, one or more steps of method 200 may be executed by any number of computing devices operating in the distributed computing system described in FIG. 1. For instance, one or more computing devices may locally perform part or all of the steps described in FIG. 2 or a cloud device may perform such steps.

At step 210, a data processing system (e.g., the analytics server 110*a* or the end-user device 140) may receive an image of one or more pre-contoured organs. The image may be a two-dimensional or a three-dimensional image and may include pixels or voxels, accordingly. As described herein, each reference to a voxel may be a reference to a pixel in cases in which the relevant image is a two-dimensional image. The image may be a CT scan of an individual that is receiving radiotherapy treatment at one or more radiation therapy clinics. The image may depict the organs and/or bone structure of the individual and may, in some cases, be contoured (e.g., labeled) to indicate which organs or other body parts are depicted in the image. For example, the image may depict the internal organs of a person's abdominal region. The different voxels of the image may be outlined or otherwise labeled with indicators of the organs they represent. For instance, the voxels may outline a person's lungs, heart, and intestines with different identifications for each of the individual organs. In some instances, the voxels may be labeled more granularly by labeling different segments of the same organ, such as different parts of the liver. In such instances, the voxels may be labeled with multiple labels indicating the organ itself and the segment of the organ that the voxel represents.

The data processing system may receive the image responsive to an individual (e.g., a technician or a doctor) uploading the image to a database of the data processing system. For instance, the physician may capture a CT scan (e.g., using a CT scanner at a radiotherapy clinic) and upload the scan to the data processing system for storage. The physician may upload the scan manually through a user selection at a user interface or the scanner may automatically upload the image. In some cases, before uploading the scan, the physician may label the scan with an outline of the different organs the scan depicts. The physician may do so by hand or by using contouring software (e.g., GRATIS, PLUNC, PRISM, etc.). The physician may label all or a portion of the scan and may do so with varying degrees of accuracy depending on the skill and level of care of the labeling physician. Upon labeling an image, the physician may upload the image to the database for storage.

The data processing system may also receive a radiotherapy treatment plan that corresponds to the respective image. The radiotherapy treatment plan may indicate the radiation dosage that is being applied to various portions of the patient depicted in the image, among other treatment attributes (e.g., field-geometry settings, dosage frequency, etc.). The data processing system may receive the radiotherapy treatment plan as a record (e.g., a document or a form) and store the plan in a database. In some cases, the data processing system may store an association (e.g., a pointer or as corresponding instances in a look-up table) between the radiotherapy treatment plan and the image indicating the plan and image are related or correspond to each other.

At step 220, the data processing system may execute a machine learning model using the image to output predicted organ labels for the plurality of voxels of the image. The machine learning model may be a random forest, a support vector machine, a neural network (e.g., a convolutional neural network), etc. The data processing system may execute the machine learning model by retrieving the image from storage and generating a feature vector representing the voxels of the image. The data processing system may apply the feature vector to the machine learning model to obtain output labels indicating the organs (or other indicators such as empty space, bones, or another body component) that the machine learning model predicts the voxels represent. For individual voxels of the image, the machine learning model may output confidence scores for different labels (e.g., labels representing different organs). The data processing system may receive the output confidence scores and identify the label that is associated with the confidence score that satisfies pre-defined criteria (e.g., the confidence score exceeds a threshold and/or is the highest confidence score of the predicted scores for the voxel) as the predicted label for the voxel. The data processing system may iteratively compare confidence scores for different voxels to determine labels for each of the voxels. Thus, the data processing system may execute the machine learning model to obtain labels for each voxel of the image.

At step 230, the data processing system may determine differences between corresponding predicted organ labels and expected organ labels for the plurality of voxels. The expected organ labels may be the labels that the technician or the data processing system used to contour the image after the image was captured and before the image was stored by the data processing system. The expected labels may be stored as metadata for the respective images. The expected labels may be treated as the ground truth or the correct labels for the voxels. The differences may be the differences in confidence scores of the expected organ label (e.g., 50%, 70%, 100%, etc.) and the predicted confidence score for the same label. The data processing system may identify the ground truth label for the voxel from the image's metadata and may determine the expected confidence score for the label to be 100%.

The data processing system may determine the differences by subtracting the corresponding confidence scores from each other. For example, the data processing system may identify a ground truth for a particular voxel to be 100% for a "lung" label. The data processing system may identify the output percentage for the lung label from the machine learning model for the same voxel to be 70%. The data processing system may determine the difference between the expected and the predicted labels by subtracting the 70% from 100% or 100% from 70%. The data processing system may determine such differences for different labels of the same voxels and/or for the different voxels of the image.

At step 240, the data processing system may determine radiation dose levels that correspond to the plurality of voxels of the image. The data processing system may determine the radiation dose levels for the voxels based on the stored radiotherapy treatment plan that corresponds to the image. The data processing system may identify the radiotherapy treatment plan based on the stored association between the plan and the image and retrieve the plan from storage. Upon retrieving the plan, the data processing system may identify the radiation dose levels that the plan calls for applying to the different organs and/or areas of the organs of the individual. The data processing system may correlate (e.g., assign) the different dose levels to the voxels of the image that represent the respective organs and/or areas to determine the radiation dose levels that correspond to the voxels.

The radiotherapy plan may be an electronic document or form. To identify the radiation dose levels from a radiotherapy treatment plan document, the data processing system may use natural language processing techniques on the document. The data processing system may use natural language processing techniques to identify the organs and/or areas of the patient that are receiving treatment and/or the radiation dose levels that are being applied to the different areas. The data processing system may then identify the voxels of the image that correspond to the respective areas to determine the radiation dose levels that are being applied to the areas the voxels represent.

In some instances, the radiotherapy treatment plan may be a stored form with designated fields for the physician to input the radiation dose levels that are being applied to the different organs and/or areas of the patient. In such instances, the data processing system may identify the designated fields and retrieve the values for the radiation dose levels from the fields. The data processing system may then identify the voxels of the image that correspond to the respective areas to determine the dose levels that are being applied to the areas the voxels represent.

In still other instances, the data processing system may determine radiation dose levels based on treatment attributes of the plan. For instance, the data processing system may identify (e.g., using natural language processing techniques or from a designated field in a form) field geometry settings that a radiotherapy machine (e.g., a linear accelerator, a proton beam machine, a cobalt-60 machine, etc.) uses to treat a patient from a radiotherapy treatment plan. Such field geometry settings may include patient positioning, patient geometry, couch position, gantry position, radiation direction, radiation magnitude, etc. The data processing system may determine radiation doses by identifying radiation magnitude and/or the directions the radiotherapy machine directed radiation during therapy and the corresponding positioning and geometry of the patient. In some cases, the data processing system may identify timestamps of the patient and gantry positioning, the radiation direction, and/or treatment strength. Based on the identified data, the data processing system may determine the lengths of time that the radiotherapy machine applied the treatment to the different portions of the individual to determine the amount of radiation or radiation dose level that was applied to the individual portions of the individual. The data processing system may determine levels of the voxels by identifying the amount of radiation that was applied to the respective organ or portions of the organ.

At step 250, the data processing system may determine weights for the plurality of voxels based on the radiation dose levels of the respective voxels. The weights may be training weights indicating the expected accuracy of the ground truth or label that was assigned to the voxel. Such weights may be especially important in situations in which a technician or physician labels the voxels by hand (e.g., using contouring software). Because technicians or physicians may use such labeling to create radiotherapy treatment plans, the technicians or physicians may be careful to accurately and precisely label voxels around areas where the radiation is being applied, for instance, and may be less careful when labeling other areas or otherwise may not label those areas at all. For example, if a physician is treating a tumor on a patient's lung, the physician may make sure to contour a CT scan of the patient correctly around the lung so any uses (e.g., determining field geometry settings for a radiotherapy machine for treatment) of the image to treat the patient may be effective and correct. In doing so, however, the physician may inaccurately contour other areas of the patient, such as the patient's intestines, or fail to label such areas completely. If inconsistently labeled images are used to train a machine learning model, the model may be incorrectly biased and/or weighted and output incorrect predictions when the model executes for new images.

To determine the weights for a voxel of the plurality of voxels, the data processing system may execute a weighting function on the radiotherapy dose level that corresponds to the voxel. For example, the data processing system may compare the radiotherapy dose level to a target radiotherapy dose in a binary weighting function. An example of such a function is below:

$$w(d) = \begin{cases} 1, & \text{if } d > d^* \\ 0, & \text{if } d \leq d^* \end{cases}$$

where d is the radiotherapy dose level of the voxel, w(d) is the weighting function, and d* is the target radiotherapy dose. As illustrated in the above function, responsive to determining the radiotherapy dose level exceeds the target radiotherapy dose, the data processing system may determine the weight for the voxel is one. Responsive to determining the radiotherapy dose level is less than or equal to the target radiotherapy dose, the data processing system may determine the weight for the voxel is zero. The data processing system may set the target radiotherapy dose to any level.

In some instances, the weighting function may be a tiered weighting function in which different weights are assigned to different dose ranges. For example, the data processing system may assign a weight of 0 to voxels that correspond to radiation dose levels under 20 Gy, a weight of 0.25 to voxels that correspond to radiation dose levels between 20 Gy and 30 Gy, a weight of 0.5 to voxels that correspond to radiation dose levels between 30 Gy and 40 Gy, a weight of 0.75 to voxels that correspond to radiation dose levels between 40 Gy and 50 Gy, and a weight of 1 to voxels that correspond to radiation dose levels that exceed 50 Gy. The data processing system may assign such weights to any number of ranges and for any ranges.

In some instances, the data processing system may be configured to select thresholds or other weighting criteria to use to weight different dosage ranges based on the planning type of organs the voxels depict (e.g., target organ, organ at risk, other organ, etc.). For example, the data processing system may identify whether contoured organs of a pre-contoured image are target organs or organs at risk from the treatment plan associated with the image. For the voxels that represent the different organs, the data processing system may retrieve the thresholds associated with the type of organ the voxels represent and compare the radiation dose levels of the voxels to the respective thresholds. Such may be advantageous, for example, when there is a high radiation dose level in an organ at risk region of the image, which may mean the organ was "sacrificed" during treatment planning (e.g., expected to receive a disproportionate amount of radiation to ensure a target organ received a sufficient amount of radiation). While the voxels depicting the organ at risk may be associated with a high radiation dosage, the organ may not be precisely contoured, so the data processing system may determine the voxels to have a weight of zero or a lower weight than other voxels. To account for sacrificed organs at risk, the data processing system may use ascending weighting thresholds for the organ at risk organ planning type in which, as radiation dosage increases above ascending thresholds, the weight increases until the radiation dosage increases above a certain threshold and the data processing system either drops the weight to zero or causes the weight for voxels with such radiation dose levels to be less than voxels representing other organs at risk and that are associated with a lower radiation dose level.

In some instances, the target radiotherapy doses or the ranges described may correspond to the location on the body that is being treated. Such may be advantageous because treating cancers in different areas of the body may require different levels of radiation. For example, breast cancer may require more radiation than cervix cancer for adequate treatment. Thus, while less radiation may be applied to treat breast cancer than to treat cervical cancer, a physician may still accurately contour CT scans for the breast cancer despite applying less radiation to the afflicted area. Accordingly, the training images may be labeled to indicate the type of cancer or another disease for which they are being used for treatment. Upon receiving or identifying the training images, the data processing may retrieve weighting criteria (e.g., thresholds and ranges) from memory based on the respective labels of the images and determine the weights for the voxels of the images based on the retrieved criteria.

In some instances, instead of outputting a binary value, the weighting function may scale based on a determined difference between the level of radiation of the respective voxel and a target level of radiation, and a scaling value. For instance, the weighting function may be:

$$w(d) = \text{sigmoid}\left(\frac{d^* - d}{d_{scale}}\right)$$

where d is the radiotherapy dose level of the voxel, w(d) is the weighting function, d* is the target radiotherapy dose, and $d_{scale}$ is a scaling value. $d_{scale}$ may be any value and may be input by a user. The weighting function may not include adjusting the difference between d* and d by $d_{scale}$ depending on how the data processing system is configured. The data processing system may apply the above function to the voxels of the image to determine weights for each of the voxels. Thus, the data processing system may train the machine learning model based on each of the voxels of the image to some degree instead of only using voxels with a radiation dosage level that exceeds a threshold.

In configurations in which the data processing system is configured to determine the radiation dosage for individual voxels based on field geometry settings that correspond to an RTTP plan of an image, the data processing system may determine the areas on the person's body in which the respective radiotherapy machine directed radiation during treatment. The data processing system may determine a weight for the corresponding voxel based on the determination. For example, the data processing system may determine a weight to be a binary value of one responsive to determining the radiotherapy machine directed radiation at an area of an individual's body and a binary value of zero responsive to determining the radiotherapy machine did not direct radiation to another area of the individual's body.

At step 260, the data processing system may train the machine learning model based on the differences and the weights for the plurality of voxels. To do so, the data processing system may determine the loss for individual voxels by assigning the determined weight for the voxel to a loss function determined based on a predicted label and a ground truth for the voxel. For example, the data processing system may execute the following formula to determine the loss for a particular voxel:

$$Loss_i = w(d_i)(l_i - l^*_i)^2$$

where Loss$^i$ is the loss for an individual voxel i, $w(d_i)$ is the weighting function, $l_i$ is the predicted organ label for the voxel i, and $l^*_i$ is the ground truth label for the voxel i. The data processing system may assign the determined weights to any stored loss functions to generate an executable loss function. The data processing system may then determine a loss for the image using the following loss function:

$$Loss_{total} = \sum_{i \in voxels} w(d_i)(l_i - l^*_i)^2$$

wherein $Loss_{total}$ is the total loss for the image. The data processing system may train the machine learning model using the weighted loss functions for individual voxels and/or the weighted loss function for the image. The data processing system may use a back propagation technique to determine a gradient for the respective loss function and update the weights and/or parameters of the machine learning model using the gradient, such as by using gradient descent techniques.

Upon being trained, the data processing system may determine an accuracy for the machine learning model by feeding the machine learning model another pre-contoured image. The data processing system may determine an accuracy for the image by comparing the output prediction labels to the ground truth prediction labels for the images and compare the accuracy to a threshold. The data processing system may iteratively feed the machine learning model training images until determining the model is accurate to a threshold, at which point the data processing system may use the machine learning model in real-time to contour images for RTTP planning.

For example, after training a machine learning model to a threshold accuracy, the data processing system may receive an image (e.g., a two-dimensional image or a three-dimensional image or model) of a scan of a person. The image may not be contoured or labeled. The data processing system may feed the image (e.g., feed characteristics of individual voxels of the image) into the machine learning model and execute the model to obtain an output of predicted labels for the individual voxels of the image. The data processing system may recreate the image in a record by drawing an outline of the different organs in the image or generating a contoured three-dimensional model according to the assigned labels. The data processing system may control or adjust the radiotherapy machine or settings of the radiotherapy machine based on the predicted output and the radiotherapy attributes.

Referring now to FIGS. 3A-3B, a non-limiting example of a weighted pre-contoured training image 300 is illustrated. The training image 300 may be a pre-contoured two-dimensional image or a three-dimensional image of a CT scan of a person that may be input into a machine learning model (e.g., as a feature vector) to train the machine learning model to contour raw (e.g., non-contoured) images. Specifically, FIG. 3A illustrates a the training image 300 including a plurality of voxels 302a-p that depict or otherwise represent corresponding portions of the individual depicted in the training image 300. The voxels 302a-p may be contoured to illustrate one or more organs or bones 304a-e of the depicted individual. As depicted, the organs or bones 304a-e may be lungs, a heart, a pelvis, a sternum, etc. Training images may illustrate or be contoured to illustrate any organs or bones of a person, in some cases including tumors, lumps or lesions on such organs or bones.

Referring now to FIG. 3B, by implementing the systems and methods described herein, a data processing system may determine weights for the voxels 302a-p of the image 300. The weights may be binary or non-binary values that the data processing system can assign to the voxels 302a-p. For example, as illustrated, the data processing system may determine weights for the voxels to be one or zero based on a weighting function. The data processing system may use such weights in a loss function to train the machine learning model to accurately contour images using backpropagation and gradient descent techniques as described herein.

Figure 4:
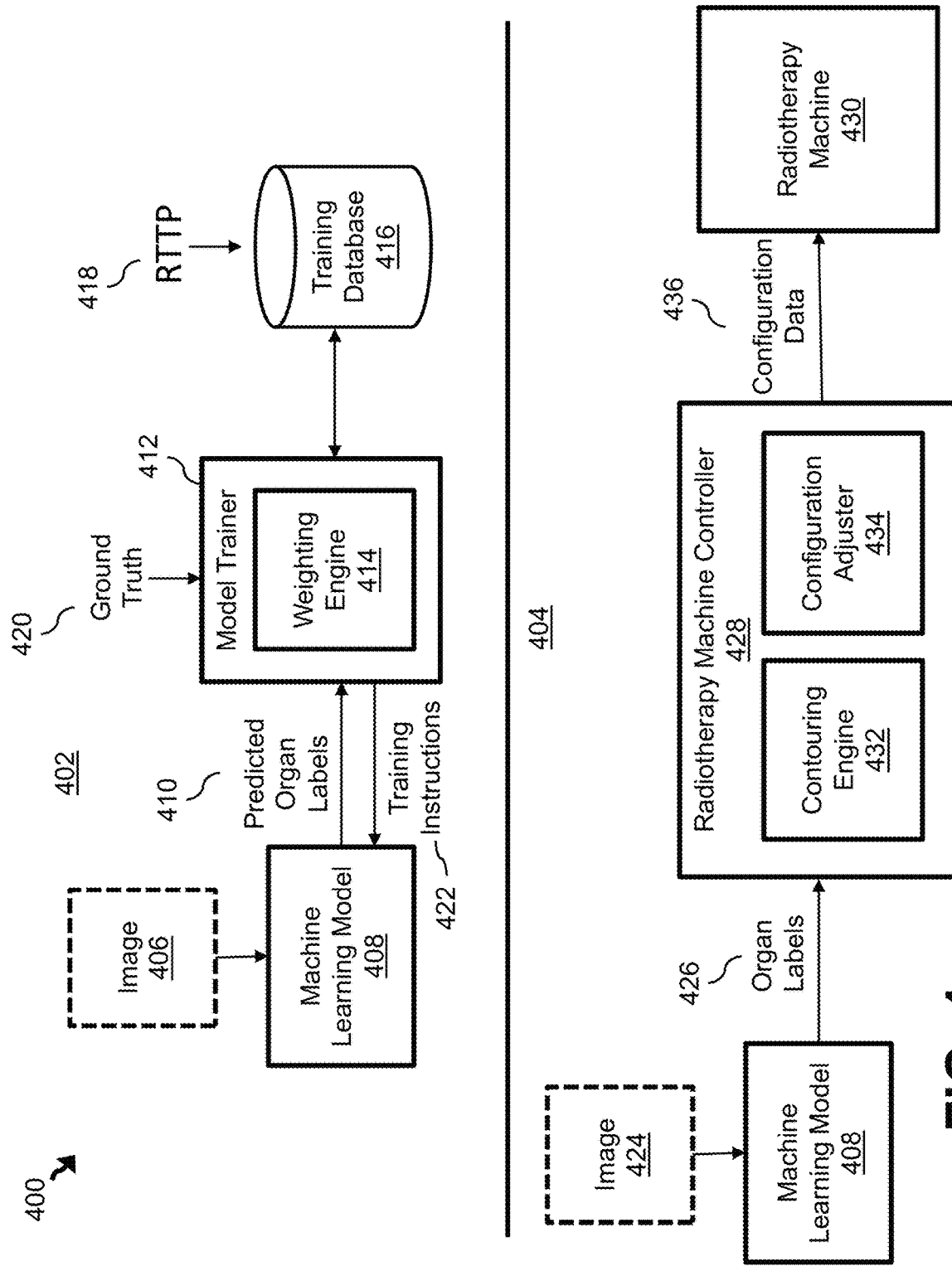
FIG. 4 illustrates an example flow diagram of another process executed in an organ contouring segmentation system, according to an embodiment.

Referring now to FIG. 4, a non-limiting example of sequences 400 for generating a training data set, using the training data set to train a machine learning model to contour organs of an image, and then using the trained machine learning model to contour an image to adjust a configuration of a radiotherapy machine is illustrated. The sequences 400 may include a sequence 402 for training a machine learning model and a sequence 404 for executing the machine learning model to contour organs of an image to control a treatment with a radiotherapy machine.

In the sequence 402, an image 406 may be input into a machine learning model 408. The image 406 may be a two-dimensional or three-dimensional image of an individual (e.g., a CT scan, an MM scan, or a PET scan or a three-dimensional model generated based on such scans) illustrating the individual's bones and/or organs and any tumor growing inside the individual. The image 406 may be a training image of a training data set (not shown) that has been labeled or contoured to indicate the organs or bones that the individual voxels of the image represent. The image 406 may be input as a feature vector with values representing characteristics (e.g., color, dimension, depth, opacity, etc.) of the voxels of the image 406. The image 406 may be inserted into the machine learning model 408 by a data processing system operating locally at a radiotherapy clinic or operating in the cloud. The machine learning model 408 may output confidence scores for one or more labels (e.g., predicted organ labels 410) for each of the voxels of the image 406 to a model trainer 412.

The model trainer 412 may comprise instructions executable by one or more processors that causes the processors to train the machine learning model 408 to contour organs in an image. The model trainer 412 may apply the image 406 to the machine learning model 408. The model trainer 412 may comprise a weighting engine 414 that is configured to determine weights for individual voxels of images based on the radiation dosage that corresponds to the respective voxel. The weighting engine 414 may receive the predicted organ labels 410 from the machine learning model 408 and an identification (e.g., a name, number, or another identifier) of the image 406. The weighting engine 414 may compare the identification to a training database 416 and identify an RTTP 418 that corresponds to the image 406 responsive to the identification of the image 406 matching an identifier on the RTTP 418. The weighting engine 414 may determine the radiation dosage of individual voxels based on the RTTP 418 and determine weights based on the radiation dosage as described herein. The weighting engine 414 may compare the predicted organ labels 410 to a ground truth 420 that indicates the correct labels for the image 406. The weighting engine 414 may generate a loss function based on determined weights and differences between the predicted organ labels 410 and the ground truth 420. The weighting engine 414 may adjust the weights or parameters of the machine learning model 408 based on the loss function (e.g., using back propagation and gradient descent techniques with) using training instructions 422. The model trainer 412 may continually apply training images similar to the image 406 to the machine learning model 408 until the machine learning model 408 is trained to an accuracy threshold percentage. Upon sufficient training, the machine learning model 408 may contour organs in images for RTTP planning.

After sufficiently training the machine learning model 408, at the sequence 404, the machine learning model 408 may be executed using an image 424 as an input. The machine learning model 408 may generate and transmit confidence scores for organ labels 426 to a radiotherapy machine controller 428. The radiotherapy machine controller 428 may comprise instructions executable by one or more processors that causes the processors to receive the confidence scores, contour the image 424 based on the confidence scores, and control a radiotherapy machine 430 based on the contoured image.

For example, the radiotherapy machine controller 428 may include a contouring engine 432 and a configuration adjuster 434. The contouring engine 432 may receive the confidence scores for organ labels 426 and determine the correct labels for individual voxels of the image 424 based on the confidence scores (e.g., based on the scores that satisfy predetermined criteria such as a satisfying a threshold or being the highest score). The configuration adjuster 434 may identify the labels from the contoured image and transmit configuration data 436 to the radiotherapy machine 430 to adjust the field geometry settings or other RTTP characteristics to treat the patient depicted in the image 424.

In one embodiment, a data processing system may determine radiation dosages and/or weights for individual voxels based on a function associated with a biological impact of doses of radiation. For example, instead of using the radiation dosage from an RTTP to determine the doses for voxels, the data processing system may measure the biological impact the radiation dosage caused within the person or receive such measurements from another source. Examples of such impacts include, but are not limited to, a change in tumor size, a change in cellular structure, a change in deoxyribonucleic acid (DNA), etc. The data processing system may measure or compare the changes against a threshold or a look-up table to either determine the radiation dosage that was applied to the affected area (e.g., each threshold may correspond to a different radiation dosage) or to determine weights for the voxels corresponding to the affected area (e.g., each threshold may correspond to a different radiation dosage or a different weight). The data processing system may use the determined radiation dosages or weights to train machine learning models to contour images as described herein.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method for training a machine learning model for automatic organ segmentation, the method comprising:
    receiving, by a processor, an image of one or more pre-contoured organs, the image comprising a plurality of voxels;
    executing, by the processor, a machine learning model using the image to output predicted organ labels for the plurality of voxels of the image;
    determining, by the processor, differences between corresponding predicted organ labels and expected organ labels for the plurality of voxels of at least one pre-contoured organ;
    determining, by the processor, radiation dose levels that correspond to the plurality of voxels of the image;
    determining, by the processor, weights for the plurality of voxels based on the radiation dose levels of the respective voxels; and
    training, by the processor, the machine learning model based on the differences and the weights for the plurality of voxels.

2. The method of claim 1, wherein determining a weight for a voxel of the plurality of voxels comprises:
    comparing, by the processor, a radiation dose level for the voxel to a threshold; and
    determining, by the processor, the weight for the voxel to be zero responsive to determining the radiation dose level does not exceed the threshold.

3. The method of claim 1, wherein determining the radiation dose levels for the plurality of voxels comprises:
    receiving, by the processor, a radiation therapy treatment plan comprising treatment attributes for a patient, the treatment attributes comprising radiation dose levels for the plurality of voxels; and
    identifying, by the processor, the radiation dose levels from the radiation therapy treatment plan.

4. The method of claim 1, wherein determining the radiation dose levels for the plurality of voxels comprises:
    receiving, by the processor, a radiation therapy treatment plan comprising treatment attributes for a patient, the treatment attributes comprising field geometry settings for a radiation therapy machine treating the patient; and
    determining, by the processor, the radiation dose levels based on the field geometry settings.

5. The method of claim 4, wherein determining the radiation dose levels based on the field geometry settings comprises:
    determining, by the processor, whether the plurality of voxels of the image correspond to an area on a body of the patient at which the radiation therapy machine directed radiation;
    wherein determining, by the processor, the weights for the plurality of voxels comprises determining, by the processor, binary weights for the identified voxels based on the determination of whether the plurality of voxels correspond to an area on a body of the patient at which the radiation therapy machine directed radiation.

6. The method of claim 1, wherein determining a weight for a voxel of the plurality of voxels comprises:
    determining, by the processor, a difference between a radiation dose level that corresponds to the voxel and a target dose level; and
    determining, by the processor, the weight by applying a sigmoid function to the difference.

7. The method of claim 6, wherein determining the weight for the voxel further comprises:
    adjusting, by the processor, the difference between the radiation dose level and the target dose level based on a scaling factor,
    wherein applying the sigmoid function to the difference comprises applying, by the processor, the sigmoid function to the adjusted difference.

8. The method of claim 1, wherein training the machine learning model comprises:
    assigning, by the processor, the determined weights to corresponding squared differences between corresponding predicted organ labels and expected organ labels for the plurality of voxels.

9. The method of claim 1, further comprising:
    receiving, by the processor, a second image;
    executing, by the processor, the trained machine learning model using the second image to obtain an output of contoured organs; and
    adjusting, by the processor, a field geometry setting of a radiotherapy machine based on the output of contoured organs.

10. The method of claim 9, wherein receiving the second image comprises receiving a three-dimensional image;
    wherein executing the trained machine learning model using the second image comprises applying, by the processor, individual voxels of the image to the trained machine learning model, and
    wherein obtaining the output of the contoured organs comprises obtaining a three-dimensional model of the contoured organs, the three-dimensional model comprising predicted labels for voxels of the three-dimensional model indicating contoured organs that correspond to the respective voxels.

11. A system for training a machine learning model for automatic organ segmentation, the system comprising:
a processor configured to execute instructions stored on a non-transitory computer-readable medium to:
receive an image of one or more pre-contoured organs, the image comprising a plurality of voxels;
execute a machine learning model using the image to output predicted organ labels for the plurality of voxels of the image;
determine differences between corresponding predicted organ labels and expected organ labels for the plurality of voxels of at least one pre-contoured organ;
determine radiation dose levels that correspond to the plurality of voxels of the image;
determine weights for the plurality of voxels based on the radiation dose levels of the respective voxels; and
train the machine learning model based on the differences and the weights for the plurality of voxels.

12. The system of claim 11, wherein the processor is configured to determine a weight for a voxel of the plurality of voxels by:
comparing a radiation dose level for the voxel to a threshold; and
determining the weight for the voxel to be zero responsive to determining the radiation dose level does not exceed the threshold.

13. The system of claim 11, wherein the processor is configured to determine the radiation dose levels for the plurality of voxels by:
receiving a radiation therapy treatment plan comprising treatment attributes for a patient, the treatment attributes comprising radiation dose levels for the plurality of voxels; and
identifying the radiation dose levels from the radiation therapy treatment plan.

14. The system of claim 11, wherein the processor is configured to determine the radiation dose levels for the plurality of voxels by:
receiving a radiation therapy treatment plan comprising treatment attributes for a patient, the treatment attributes comprising field geometry settings for a radiation therapy machine treating the patient; and
determining the radiation dose levels based on the field geometry settings.

15. The system of claim 14, wherein the processor is configured to determine the radiation dose levels based on the field geometry settings by:
determining whether the plurality of voxels of the image correspond to an area on a body of the patient at which the radiation therapy machine directed radiation; and
determining binary weights for the identified voxels based on the determination of whether the plurality of voxels correspond to an area on a body of the patient at which the radiation therapy machine directed radiation.

16. The system of claim 11, wherein the processor is configured to determine a weight for a voxel of the plurality of voxels by:
determining a difference between a radiation dose level that corresponds to the voxel and a target dose level; and
determining the weight by applying a sigmoid function to the difference.

17. The system of claim 16, wherein the processor is configured to determine the weight for the voxel by:
adjusting the difference between the radiation dose level and the target dose level based on a scaling factor,
wherein the processor is configured to apply the sigmoid function to the difference by applying the sigmoid function to the adjusted difference.

18. The system of claim 11, wherein the processor is configured to train the machine learning model by:
assigning the determined weights to corresponding squared differences between corresponding predicted organ labels and expected organ labels for the plurality of voxels.

19. The system of claim 11, wherein the processor is configured to:
receive a second image;
execute the trained machine learning model using the second image to obtain an output of contoured organs; and
adjust a field geometry setting of a radiotherapy machine based on the output of contoured organs.

20. The system of claim 19, wherein the processor is configured to receive the second image by receiving a three-dimensional image;
wherein the processor is configured to execute the trained machine learning model using the second image by applying individual voxels of the image to the trained machine learning model, and
wherein the processor is configured to obtain the output of the contoured organs by obtaining a three-dimensional model of the contoured organs, the three-dimensional model comprising predicted labels for voxels of the three-dimensional model indicating contoured organs that correspond to the respective voxels.

* * * * *